United States Patent [19]

Schaumann et al.

[11] Patent Number: 4,704,381

[45] Date of Patent: Nov. 3, 1987

[54] USE OF ADENOSINE DERIVATIVES AS ANTI-ALLERGIC COMPOUNDS AND PHARMACEUTICAL COMPOSITIONS CONTAINING THEM

[75] Inventors: Wolfgang Schaumann, Heidelberg; Otto-Henning Wilhelms, Weinheim-Rittenweier; Androniki Roesch, Mannheim; Wolfgang Kampe, Heddesheim, all of Fed. Rep. of Germany

[73] Assignee: Boehringer Mannheim GmbH, Mannheim, Fed. Rep. of Germany

[21] Appl. No.: 701,139

[22] Filed: Feb. 13, 1985

[30] Foreign Application Priority Data

Feb. 23, 1984 [DE] Fed. Rep. of Germany ....... 3406533

[51] Int. Cl.$^4$ .................... A61K 3/70; C07H 19/06
[52] U.S. Cl. ................................ 514/46; 536/26
[58] Field of Search ............... 514/46, 45; 536/26

[56] References Cited

U.S. PATENT DOCUMENTS

| | | | |
|---|---|---|---|
| 3,590,029 | 6/1971 | Koch et al. | 536/26 |
| 3,851,056 | 11/1974 | Stork et al. | 514/46 |
| 4,501,735 | 2/1985 | Trivedi et al. | 514/46 |

FOREIGN PATENT DOCUMENTS

| | | | |
|---|---|---|---|
| 0061001 | 9/1982 | European Pat. Off. | 514/46 |
| 2055160 | 5/1972 | Fed. Rep. of Germany | 514/46 |
| 2139107 | 2/1973 | Fed. Rep. of Germany | 536/26 |
| 0145898 | 9/1982 | Japan | 514/46 |

*Primary Examiner*—Johnnie R. Brown
*Assistant Examiner*—John W. Rollins, Jr.
*Attorney, Agent, or Firm*—Felfe & Lynch

[57] ABSTRACT

The present invention is concerned with the use of adenosine derivatives for the treatment of allergic diseases, as well as for bronchosphatic and broncho-constrictive reactions brought about by inflammation. The above adenosine derivatives can be used alone or together with xanthine derivatives. The invention is further concerned with compositions containing compounds of adenosine derivatives and optionally compounds of xanthine derivatives together with appropriate pharmaceutical carriers.

7 Claims, 1 Drawing Figure

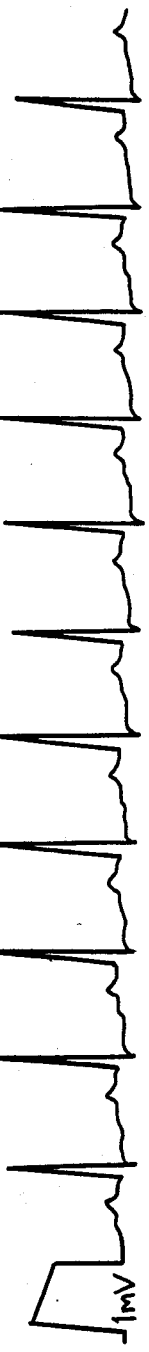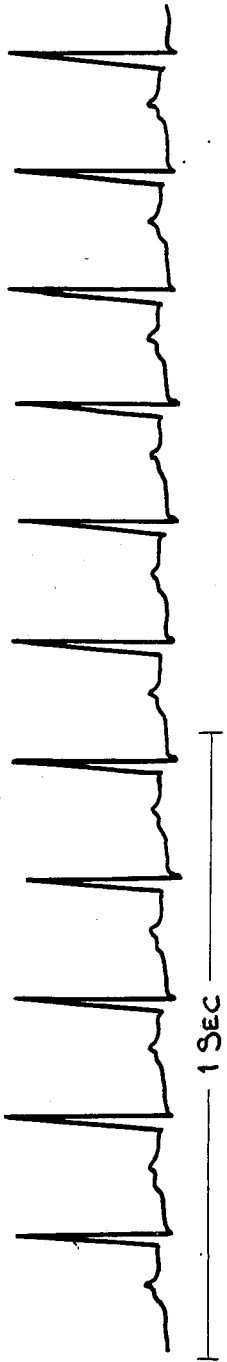

USE OF ADENOSINE DERIVATIVES AS ANTI-ALLERGIC COMPOUNDS AND PHARMACEUTICAL COMPOSITIONS CONTAINING THEM

The present invention is concerned with the use of adenosine derivatives as anti-allergic compounds and with pharmaceutical compositions containing them.

It is known that adenosine and numerous derivatives thereof possess a large variety of pharmacological activities. Besides a dilation of the blood vessels, lowering of the blood pressure, bradycardia, atrioventricular (AV) blocking and an inhibition of lipolysis, actions on the immune system have also been described. Furthermore, it is known that adenosine and an N-monosubstituted derivative thereof, namely phenylisopropyladenosine (L-PIA), potentiates the liberation, initiated by antigen, of histamine and other mediators, such as SRS-A (slow reacting substance of anaphylaxis) from isolated mast cells and lung tissue. Therefore, according to the present state of knowledge, adenosine and L-PIA act pro-allergically.

It was, therefore, extraordinarily surprising to find that other adenosine derivatives already investigated because of their blood vessel-dilating, blood pressure-lowering and lipolysis-inhibiting properties display an anti-allergic action in vitro and in vivo. This can be determined relatively easily by investigations of the liberation of SRS-A from lung tissue sample caused by antigen.

Therefore, it is an object of the present invention to use adenosine derivatives which display an inhibition of the liberation of SRS-A for the treatment of allergic diseases, as well as of bronchospastic and broncho-constrictive reactions due to inflammation.

The effective compounds according to the present invention are adenosine derivatives of the general formula:

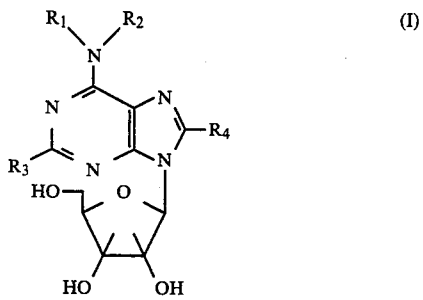

(I)

wherein $R_1$ and $R_2$, which can be the same or different, are straight-chained or branched alkyl radicals which can be substituted one or more times by hydroxyl, alkoxycarbonyl or alkoxy groups, by phenalkyl or alkyl-substituted amino groups, whereby the phenyl moiety can also be substituted, by aryl, heteroaryl or aryloxy radicals optionally substituted one or more times by hydroxyl, alkoxy, alkyl, trifluoromethyl, halogen, amino or methylsulphonamino, or by cycloalkyl, which can be annelated with an aryl ring, or $R_1$ and $R_2$ are straight-chained or branched alkenyl radicals or $R_1$ and $R_2$ are saturated or unsaturated cyclic aliphatic radicals which can be annelated with an aryl ring, or $R_1$ and $R_2$, together with the nitrogen atom to which they are attached, can form a heterocyclic ring which can optionally be interrupted by a further oxygen, sulphur or nitrogen atom, which nitrogen atom can be substituted by alkyl or aralkyl, $R_3$ is a hydrogen or halogen atom, a hydroxyl group, an alkoxy, morpholino or piperidino radical or an amino group which can optionally be substituted by alkyl or optionally substituted aralkyl and $R_4$ is a hydrogen or halogen atom or a morpholino or piperidino radical or an amino group optionally substituted by alkyl or aralkyl; and one of the symbols $R_1$ and $R_2$ can also represent a hydrogen atom, with the proviso that the other symbol is not a phenylisoprpyl radical; as well as the pharmacologically compatible salts thereof.

The majority of the compounds encompassed by general formula (I) are known (see Federal Republic of Germany Patent Specifications Nos. 16 70 077; 16 70 175; 16 70 265; 21 48 838; 21 57 036; 22 44 328; 23 38 705; 23 38 963 and 24 26 682) or can be prepared according to generally known methods such as are described in the above-mentioned Patent Specifications.

New compounds according to the present invention are adenosine derivatives of the general formula:

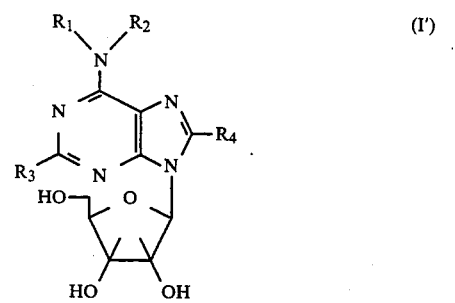

(I')

wherein $R_1$ and $R_2$, which can be the same or different, are straight-chained or brached alkyl radicals which can be substituted one or more times by hydroxyl, alkoxycarbonyl, or alkoxy radicals, by phenalkyl or alkyl-substituted amino groups, whereby the phenyl moiety can also be substituted, by aryl, heteroaryl or aryloxy radicals optionally substituted one or more times by hydroxyl, alkoxy, alkyl, trifluoromethyl, halogen, amino or methylsulphonamino, or by cycloalkyl, which can be annelated with an aryl ring; or $R_1$ and $R_2$ are straight-chained or branched alkenyl radicals; or $R_1$ and $R_2$ are saturated or unsaturated cyclic aliphatic radicals which can be annelated with an aryl ring; or $R_1$ and $R_2$, together with the nitrogen atom to which they are attached, can form a heterocyclic ring which is optionally interrupted by a further oxygen, sulphur or nitrogen atom, which nitrogen atom can be substituted by alkyl or aralkyl, $R_3$ is hydroxy, alkoxy, halogen, morpholino, piperidino or an amino group which can optionally be substituted by alkyl or optionally substituted aralkyl and $R_4$ is halogen, morpholino, piperidino or an amino group optionally substituted by alkyl or aralkyl and one of the symbols $R_3$ and $R_4$ can also be hydrogen, as well as their pharmacologically acceptable salts.

Preferred new compounds are those wherein $R^1$ is a hydrogen atom or a $C_1$-$C_8$ alkyl or hydroxyethyl radical, $R_2$ is a hydrogen atom or a $C_1$-$C_8$ alky,, benzyl, hydroxyethyl or cyclohexyl radical or $R_1$ and $R_2$, together with the nitrogen atom to which they are attached, form a piperidiono or morpholino ring, $R_3$ is a hydrogen atom, an amino group or a benzyl amino radical optionally substituted by a methyl radical, or is a morpholino or piperidino radical and $R_4$ is a benzylamino, morpholino or piperidino radical and, when $R_3$ is a morpholino or piperidino radical, $R_4$ can also be a hydrogen atom.

Especially preferred new compounds are those in which $R_4$ is a halogen atom or a morpholino or piperidino radical or an amino group optionally substituted by alkyl or aralkyl.

In general, compounds of general formula (I) which are preferred according to the present invention are those in which the N(6)-position is disubstituted, i.e. $R_1$ and $R_2$ are not hydrogen atoms.

The aryloxy, aryl and heteroaryl radicals of the substituents $R_1$ and $R_2$ or mono- or bicyclic.

By aryl there is preferably to be understood phenyl or naphthyl. An aralkyl substituent in the definitions of $R_1$, $R_2$, $R_3$ and $R_4$ is preferably a benzyl or phenylisopropyl radical.

By saturated cyclic aliphatic radicals in the definitions of $R_1$ and $R_2$ are to be understood radicals with 3 to 7 carbon atoms, especially cyclopropyl, cyclopentyl, cyclohexyl and cycloheptyl radicals. Cyclohexenyl and cycloheptenyl radicals are preferred as unsaturated cyclic aliphatic radicals.

The cyclic aliphatic radicals can be annelated with an aryl radical, preferably with a phenyl radical, indane, tetraline and benzocyclobutane rings being preferred. As heteroaryl radicals, the furanyl, thiophenyl and pyridyl radicals are preferred. All these above-mentioned aryl and heteroaryl radicals can be unsubstituted or can carry one or more of the following substituents: alkyl, alkenyl, alkoxy, alkylthio, trifluoromethyl, hydroxyl, halogen, nitro, aminocarbonyl, alkoxycarbonyl or aminosulphonyl.

All the mentioned alkyl radicals contain up to 10 and preferably up to 8 carbon atoms, for example methyl, ethyl, n-propyl, isopropyl, n-butyl, isobutyl, tert.-butyl, pentyl, hexyl and 1,5-dimethyl-n-hexyl radicals. A methyl or ethyl radical is preferred as a substituent of the aryl and heteroaryl radicals.

Alkoxy radicals contain up to 6 and preferably up to 4 carbon atoms, methoxy, ethoxy, isopropoxy and n-propoxy radicals being especially preferred.

Alkenyl radicals contain 3 to 8 and preferably 3 to 6 carbon atoms, the allyl and butenyl radicals being preferred.

For the case in which $R_1$ and $R_2$, together with the nitrogen atom to which they are attached, form a heterocycle, by this there are to be understood ring systems with 3 to 8 carbon atoms, the dimethyleneimino, trimethyleneimino, tetramethyleneimino, pentamethyleneimino and hexamethyleneimino rings being preferred. These ring systems can be interrupted by oxygen, sulphur or an additional nitrogen atom, which nitrogen atom can be substituted by a lower alkyl radical or by a benzyl radical. Preferred ring systems are morpholine, thiamorpholine and piperazine.

By halogen there is preferably to be understood fluorine, chlorine and bromine.

ACTIVITY TESTING OF ADENOSINE DERIVATIVES IN VIVO AND IN VITRO

A. Inhibition in vivo of bronchospasm in guinea pigs caused by antigen

Bronchospasm in guinea pigs caused by antigen is a typical model for the spasms in humans initiated by antigen. Under the following experimental conditions, phenylisopropyladenosine (PIA) was compared with one of the compounds according to the present invention (BM 1.189) in this experimental model on guinea pigs and the results obtained are summarised in the following Table 1.

Influence of BM 11.189 and TH 162 (L-PIA) on allergically-caused bronchospasm on passively sensitised guinea pigs Method:

H. Konzett and R. Rössler, Versuchsanordnung zu Untersuchungen an der Bronchialmuskulatur, Naunyn-Schmiedebergs Arch. exp. Path. Pharmak., 195, 71–74/1940; H. O. J. Collier, J. S. Holgate and M. Schachter, The Bronchorestrictor action of bradykinin in the guinea pig, Brit. J. Pharmacol., 15, 290/1960.

Obtaining antiserum and sensitisation

For obtaining antiserum, male albino guinea pigs were sensitised with an emulsion which consisted of equal parts of ovalbumin (5 mg./kg. in 0.9% sodium chloride solution) and complete Freund's adjuvant. The antiserum was obtained 4 weeks thereafter by canulation of the abdominal aorta on animals narcotised with penthrane and subsequently stored at $-18°$ C. 24 hours before the actual experiment, guinea pigs were passively sensitised by the intravenous adminitration of 1.5 ml. antiserum dilution/kg. (diluted 1:50 with 0.9% sodium chloride solution).

Experimental protocol for the measurement of the bronchospasm

According to the modification by Collier et al. (1960) of the Konzett-Rössler method (1940), passively sensitised guinea pigs under sodium pentobarbital narcosis (40 mg./kg. i.p.) were, after insertion of a cannula into the trachea and of a further cannula into the jugular vein, attached to a positive pressure ventilator. An air volume of 7 to 15 ml. was applied 72 times a minute to the animals by means of the positive pressure ventilator. The antigen-caused bronchospasm was induced by the intravenous administration of 1 mg. ovalbumin so that the respiration volume could not flow completely into the lungs and partly flowed off through a side arm via a valve. This air volume was measured indirectly as flow velocity with the help of a thermo-element and served as a measurement for the strength of the bronchospasm. The administration of the test substrates took place into the jugular vein 5 minutes before the antigen injection.

The substance-caused influence on the antigen-induced bronchospasm was determined by comparison of treated animals with control groups for the time point 3 minutes after antigen administration and the inhibition action calculated as a percentage. The evaluation was carried out according to the following formula:

$$\% \text{ bronchospasm} = \frac{X - B}{M - B} \times 100$$

$X - B$ is the bronchospasm observed after antigen administation and measured in mm. curve deflection $M - B$ is the maximum bronchospasm achievable by clamping the tracheal cannula measured in mm. curve deflection $B$ is the initial value in mm. curve deflection.

The significance of these results was confirmed statistically with the t test.

TABLE 1

| test substance | dosage mg/kg i.v. | % inhibition of the bronchospasm |
|---|---|---|
| TH 162 (L-PIA) | 0.5 | −17 |
|  | 5.0 | 20 |
| BM 11.189 | 0.5 | 40 |

Results:

After 0.5 mg./kg. i.v., BM 11.189 brings about a 40% significant inhibition of the antigen-caused bronchospasm on the passively sensitised guinea pig. In contradistinction thereto, L-PIA was ineffective in the case of the same manner of administration in the same experimental arrangement after 0.5 and 5.0 mg./kg.

B. Inhibition of the liberation of SRS-A caused by antigen from guinea pig lung tissue in vitro.

For the in vitro investigation of the compounds according to the invention, the liberation of SRS-A caused by antigen from passively sensitised lung tissue of guinea pigs was investigated. The investigation was carried out by the following method:

Freshly removed lung tissue which had previously been washed substantially free of blood in situ with Krebs buffer (pH 7.4) was comminuted with a McIlwain tissue chopper, washed with Krebs buffer (pH 7.4) and incubated for 1 hour at ambient temperature with a 1:50 dilution of a homologous anti-ovalbumin antiserum. The antiserum was previously produced in guinea pigs by repeated injection of ovalbumin (crystallised twice), with the addition of complete Freund's adjuvant, according to the method of G. E. Davies and T. P. Johnstone (Quantitative studies on anaphylaxis in guinea pigs passively sensitised with homologous antibody, Inter. Arch. Allergy, 41, 648–654/1971). Until used, the antiserum was stored undiluted at −18° C.

Subsequently, the passively sensitised tissue was washed twice with Krebs buffer (pH 7.4) and samples each of about 400 mg. incubated in Krebs buffer with and without the addition of test substance (on average $3 \times 10^{-5}$M) for 30 minutes before the antigen-induced liberation of SRS-A was initiated by the addition of ovalbumin solution (end concentration 10 mcg./ml.). The liberation reaction was stopped after 15 minutes by the addition of an equal volume of ice-cold tyrode solution (pH 8.0). After separation of the tissue by centrifuging, the supernatants were stored at −18° C. until the measurement of their SRS-A content in the ileum bioassay.

The ileum bioassay was carried out in a partly automated process in superfusion on pieces of ileum from untreated guinea pigs. Th working buffer was tyrode solution (pH 8.0) with the addition of atropine ($2 \times 10^{-7}$M) and mepyramine ($10^{-6}$M).

The superfusion time for the sample was 3 minutes, followed by a rinsing phase of 6 minutes. As a measure for the content of SRS-A, there was used the maximum contraction amplitude (K). After stimulation with ovalbumin, the SRS-A content in the sample supernatants increased on average by the factor 3 in comparison with the buffer control.

The substance-caused inhibitory action in percent to the "specific" antigen-induced SRS-A liberation was determined as follows:

$$\frac{(K \text{ liberation with substance}) - (K \text{ buffer control})}{(K \text{ liberation without substance}) - (K \text{ buffer control})}$$

Results:

In the upper part of the following Table 2, there are summarised the results with L-PIA and adenosine which, in the manner known from the literature, promote the antigen-caused liberation of SRS-A. The promotion of the SRS-A liberation was substantially equally strong in the concentration range of $10^{-5}$ to $10^{-7}$M.

BM 11.189, which was tested in more detail, and numerous other adenosine derivatives showed a more or less marked inhibition of the SRS-A liberation (see the following Table 2).

TABLE 2

Influence of adenosine derivatives on the antigen-caused liberation of SRS-A from guinea pig lung tissue

| test compound | $n^{conc.}_{(mole/liter)}$ | liberation of SRS-A in % of the control |
|---|---|---|
| L-PIA | 24 $10^{-6}$M | 164 |
| adenosine | 7 $10^{-3}$M | 194 |
|  | $3 \times 10^{-5}$M |  |
| EF 1191 | 3 | 85 |
| EF 1177 | 3 | 79 |
| EF 1183 | 3 | 63 |
| EF 1056 | 3 | 79 |
| EF 1045 | 3 | 76 |
| EF 1057 | 3 | 71 |
| EF 1112 | 3 | 81 |
| EF 1114 | 3 | 85 |
| EF 1109 | 1 | 77 |
| EF 1052 | 1 | 71 |
| EF 1137 | 1 | 73 |
| EF 1143 | 1 | 80 |
| EF 1141 | 1 | 84 |
| BM 11.189 | 13 | 84 |
| BM 11.393 | 9 | 47 |
| BM 11.308 | 4 | 81 |
| BM 11.148 | 4 | 76 |
| BM 11.366 | 3 | 79 |
| BM 11.373 | 3 | 58 |
| BM 11.276 | 3 | 81 |
| BM 11.288 | 4 | 90 |
| BM 11.250 | 3 | 91 |
| BM 11.020 | 3 | 94 |
| BM 11.021 | 1 | 94 |
| BM 11.258 | 1 | 99 |
| BM 11.407 | 3 | 63 |
| BM 11.240 | 3 | 86 |
| BM 11.243 | 3 | 61 |
| BM 11.256 | 3 | 76 |
| BM 11.354 | 3 | 68 |
| BM 11.368 | 3 | 69 |
| BM 11.098 | 1 | 68 |
| BM 11.112 | 1 | 86 |
| BM 11.208 | 1 | 89 |
| BM 11.356 | 1 | 75 |
| BM 11.280 | 1 | 74 |
| BM 11.238 | 1 | 89 |
| BM 11.184 | 1 | 88 |
| BM 11.323 | 1 | 85 |
| KA 230 | 3 | 65 |
| KA 133 | 3 | 65 |
| KA 339 | 3 | 80 |
| KA 196 | 3 | 74 |
| KA 441 | 1 | 71 |
| KA 373 | 1 | 88 |
| KA 37 | 1 | 77 |
| BM 12.235 | 5 | 48 |
| BM 12.350 | 4 | 54 |
| BM 12.357 | 6 | 36 |
| BM 12.341 | 4 | 97 |
| BM 12.046 | 6 | 89 |
| BM 12.257 | 3 | 61 |
| BM 12.290 | 3 | 64 |
| BM 12.399 | 3 | 73 |

TABLE 2-continued

Influence of adenosine derivatives on the antigen-caused liberation of SRS-A from guinea pig lung tissue

| test compound | $n^{conc.}_{(mole/liter)}$ | liberation of SRS-A in % of the control |
|---|---|---|
| BM 12.400 | 3 | 64 |
| BM 12.359 | 3 | 80 |
| BM 12.356 | 3 | 80 |
| BM 12.258 | 3 | 85 |
| BM 12.194 | 1 | 87 |
| BM 12.075 | 1 | 76 |
| BM 12.250 | 1 | 77 |
| BM 12.151 | 1 | 86 |
| TH 454 | 3 | 71 |
| TH 223 | 1 | 89 |
| TH 101 | 1 | 77 |
| TH 246 | 1 | 79 |
| TH 142 | 1 | 77 |
| TH 499 | 1 | 88 |

A summary of the tested compounds according to general formula (I) is given in the following Table 3:

TABLE 3

| No. | Code No. | $R_1$ | $R_2$ | $R_3$ | $R_4$ | m.p./°C. |
|---|---|---|---|---|---|---|
| 1 | EF 1191 | H | —CH₂—C₆H₅ (benzyl) | —NH—CH₂—C₆H₅ | —NH—CH₂—C₆H₅ | 127–128 |
| 2 | EF 1177 | | tetrahydropyranyl (O-ring) | morpholino | morpholino | 199–200 |
| 3 | EF 1183 | —CH₂—CH₂—OH | —CH₂—CH₂—OH | piperidino | piperidino | 156–158 |
| 4 | EF 1056 | H | —CH(CH₃)₂ | H | H | 102–104 |
| 5 | EF 1045 | H | —(CH₂)₃—CH₃ | H | H | 169–170 |
| 6 | EF 1057 | H | —C(CH₃)₃ | H | H | 118–120 |
| 7 | EF 1112 | H | —(CH₂)₂—NH—C₂H₅ | H | H | 258–259 (decomp.) |
| 8 | EF 1114 | | cyclohexyl | —NH₂ | —NH—CH₂—C₆H₅ | 172–173 |
| 9 | EF 1109 | H | —(CH₂)₂—NH—CH(CH₃)—CH₂—C₆H₅ | H | H | 102–104 |
| 10 | EF 1052 | H | 2-indanyl | H | H | 164–165 |
| 11 | EF 1137 | H | —CH₂—cycloheptyl | H | H | 146–147 |

TABLE 3-continued

| No. | Code No. | R₁ | R₂ | R₃ | R₄ | m.p./°C. |
|---|---|---|---|---|---|---|
| 12 | EF 1143 | H | —CH₂—(2-hydroxyphenyl) | H | H | 174–176 |
| 13 | EF 1141 | H | —CH(cyclopentyl)(phenyl) | H | H | amorphous |
| 14 | BM 11.189 | cyclohexyl | —CH₂—CH=CH₂ | H | H | 114–116 |
| 15 | BM 11.393 | cyclopentyl | —CH₂—(4-methoxyphenyl) | H | H | 109–111 |
| 16 | BM 11.308 | cyclopentyl | —CH₂—CH(OH)—CH₂—O—phenyl | H | H | 133–134 |
| 17 | BM 11.148 | cyclohexyl | —CH₂—CH(CH₃)₂ | H | H | amorphous |
| 18 | BM 11.366 | 3-pyridyl-CH₂— | —CH₂—CH(CH₃)₂ | H | H | 110–113 |
| 19 | BM 11.373 | cyclopentyl | —CH₂—(2,6-dimethylpyridyl) | H | H | 227–228 |

TABLE 3-continued

| No. | Code No. | R₁ | R₂ | R₃ | R₄ | m.p./°C. |
|---|---|---|---|---|---|---|
| 20 | BM 11.276 | cyclohexyl | —CH₂—CH(OH)—CH₃ | H | H | amorphous |
| 21 | BM 11.288 | (CH₃)₂—CH—CH₂— | —CH₂—C₆H₅ | H | H | 192–193 |
| 22 | BM 11.250 | 1-methyl-tetrahydronaphthyl | —CH₂—CH(CH₃)₂ | H | H | 172–174 |
| 23 | BM 11.020 | —CH₃ | —CH₃ | —C₆H₄(CH₃)—CH₂—NH— | H | 139–140 |
| 24 | BM 11.021 | H | cyclohexyl | morpholino (N-linked) | H | 239–240 |
| 25 | BM 11.258 | CH₂=CH—CH₂— | —CH₂—C₆H₃(CH₃)₂ | H | H | amorphous |

TABLE 3-continued
| No. | Code No. | R₁ | R₂ | R₃ | R₄ | m.p./°C. |
|---|---|---|---|---|---|---|
| 26 | BM 11.407 | 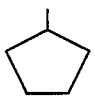 | 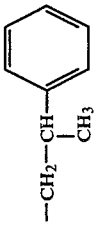 | H | H | 79-82 |
| 27 | BM 11.240 | (CH₃)₂CH—CH₂— | —CH₂—CH—CH₃ | H | H | 171-172 |
| 28 | BM 11.243 |  | —CH₂—CH(CH₃)₂ | H° | H | 138-140 |
| 29 | BM 11.256 | (CH₃)₂CH— | 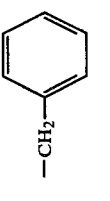 | H | H | 128-130 |
| 30 | BM 11.354 | (CH₃)₂CH—CH₂— | 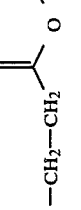 | H | H | 130-132 |
| 31 | BM 11.368 | (CH₃)₂—CH—CH₂— | 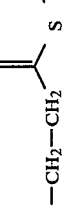 | H | H | 166-167 |
| 32 | BM 11.098 | H | 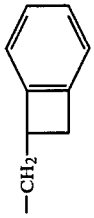 | H | H | 183-185 |
| 33 | BM 11.112 | H | 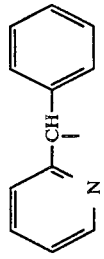 | H | H | amorphous |

TABLE 3-continued

| No. | Code No. | R₁ | R₂ | R₃ | R₄ | m.p./°C. |
|---|---|---|---|---|---|---|
| 34 | BM 11.208 | cyclohexyl | −CH₂−C=CH₂ with CH₃ | H | H | 110−112 |
| 35 | BM 11.356 | cyclohexyl | −CH₂−CH₂−(furan) | H | H | 160−162 |
| 36 | BM 11.280 | 1,2,3,4-tetrahydronaphthyl | −CH₃ | H | H | 168−170 |
| 37 | BM 11.238 | cyclohexyl | −CH₂−N(piperidinyl-benzyl) | H | H | 193−194 |
| 38 | BM 11.184 | cyclohexyl | −CH₂−CH=CH−CH₃ | H | H | 112−114 |
| 39 | BM 11.323 | cyclohexyl | −(CH₂)₃−phenyl | H | H | 134−136 |
| 40 | KA 230 | H | (CH₃)₂CH−(CH₂)₃−CH−CH₃ | H | H | 79−82 |
| 41 | KA 133 | H | (CH₃)₂CH−(CH₂)₃−CH−CH₃ | Cl | H | 90−92 |
| 42 | KA 339 | H | −CH₂−CH₂−O−(2-methoxyphenyl) | H | H | 185−187 |

TABLE 3-continued
| No. | Code No. | R₁ | R₂ | R₃ | R₄ | m.p./°C. |
|---|---|---|---|---|---|---|
| 43 | KA 196 | H |  | Cl | H | 132–134 |
| 44 | KA 441 | H | 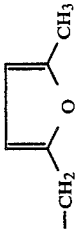 | H | H | 180–182 |
| 45 | KA 372 | H | —CH₂—CH—CH₃<br>              \|<br>             OH | H | H | 242–244 |
| 46 | KA 37 | H | 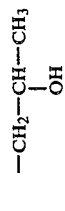 | H | H | 102–104 |
| 47 | BM 12.235 |  | 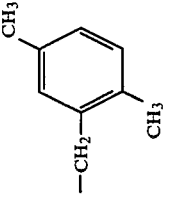 | H | H | 165–166 |
| 48 | BM 12.350 |  | 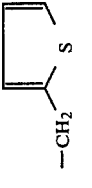 | H | H | 98–100 |
| 49 | BM 12.357 |  |  | H | H | 123–125 |
| 50 | BM 12.341 | —CH₂—C₆H₅ | —CH₂—C₆H₅ | H | H | 175–177 |

TABLE 3-continued

| No. | Code No. | R₁ | R₂ | R₃ | R₄ | m.p./°C. |
|---|---|---|---|---|---|---|
| 51 | BM 12.046 | H | -CH₂-(4-Cl, 2-OCH₃-phenyl) | H | H | 168-169 |
| 52 | BM 12.257 | -CH₂-phenyl | -CH₂-CH(CH₃)₂ | H | H | 50 (sinters) |
| 53 | BM 12.290 | -CH₂-(2,4-dimethylphenyl) | -CH₂-CH(CH₃)₂ | H | H | 65 (sinters) |
| 54 | BM 12.399 | -CH₂-cyclopentyl | -CH₂-phenyl | H | H | 70 (sinters) |
| 55 | BM 12.400 | -CH₂-cyclohexyl | -CH₂-phenyl | H | H | 99-100 |
| 56 | BM 12.359 | -CH₂-(2-thienyl) | -CH₂-CH(CH₃)₂ | H | H | 115-120 |
| 57 | BM 12.356 | -CH₂-(2-furyl) | -CH₂-CH(CH₃)₂ | H | H | 55 (sinters) |

TABLE 3-continued

| No. | Code No. | R$_1$ | R$_2$ | R$_3$ | R$_4$ | m.p./°C. |
|---|---|---|---|---|---|---|
| 58 | BM 12.258 | cyclohexyl-CH(H)– | 2,4-di(CH$_3$)-benzyl (–CH$_2$–C$_6$H$_3$(CH$_3$)$_2$) | H | H | 170–172 |
| 59 | BM 12.194 | cycloheptyl | –CH$_2$–CH(CH$_3$)$_2$ | H | H | 70–75 (sinters) |
| 60 | BM 12.075 | H | 3-(NH–SO$_2$–CH$_3$)-benzyl | H | H | 192 (decomp.) |
| 61 | BM 12.250 | H | –(CH$_2$)$_3$–O–(1-naphthyl) | H | H | 123–125 |
| 62 | BM 12.151 | H | –(CH$_2$)$_5$–COOC$_2$H$_5$ | H | H | 98–100 |
| 63 | TH 454 | –CH$_3$ | –CH$_3$ | H | piperidin-1-yl | 183–184 |
| 64 | TH 223 | –CH$_3$ | –CH$_3$ | H | H | 180–182 |
| 65 | TH 101 | H | –CH$_2$–CH=CH$_2$ | H | H | 165–167 |
| 66 | TH 246 | H | 3-Cl-benzyl (–CH$_2$–C$_6$H$_4$–Cl) | H | H | 168–169 |

TABLE 3-continued
| No. | Code No. | $R_1$ | $R_2$ | $R_3$ | $R_4$ | m.p./°C. |
|---|---|---|---|---|---|---|
| 67 | TH 142 | H | 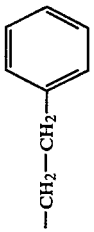—CH$_2$—CH$_2$— | H | H | 167-168 |
| 68 | TH 499 | H | —CH$_2$—CH$_2$—N(CH$_3$)$_2$ | H | H | 131-133 |

INFLUENCE OF XANTHINE DERIVATIVES ON THE ADENOSINE ACTION

It is known that theophylline and other xanthine derivatives inhibit or annul the typical actions of adenosine and of its derivatives, for example their circulatory effects. It is assumed that this is due to a blocking of the corresponding adenosine receptors by the xanthine derivatives because these compounds are structurally similar to adenosine (cf. R. F. Bruns, Pharmacol., 30, 325-353/1981; R. F. Bruns et al., Proc. Nat. Acad. Sci. USA, 80, 2077-2080/1983).

Surprisingly, we have been able to show that theophylline and other xanthine derivatives admittedly block the circulatory actions of the compounds of general formula (I) according to the present invention but not the anti-allergic action of these compounds. On the contrary, we have found that theophylline, which itself possesses an anti-allergic effectiveness, strengthens the anti-allergic action of the compounds according to the present invention. In the following Table 4, this is demonstrated on the basis of the influencing of the SRS-A liberation from lung tissue of guinea pigs, the investigations having been carried out analogously to the methods described hereinbefore under part B.

For testing the combined inhibiting action of BM 11.189 with theophylline, there are chosen the most unfavourable case of an especially strongly antigen-caused SRS-A liberation with the addition of L-PIA. As is known, L-PIA potentiates the antigen-caused SRS-A liberation, like adenosine (cf. also Table 1).

TABLE 4

Theophylline antagonises the promotion of SRS-A liberation by L-PIA and strengthens the inhibition by BM 11.189

| test substance | SRS-A in % of the control | |
|---|---|---|
| | without theophylline | with $10^{-3}M$ theophylline |
| L-PIA ($10^{-6}M$) | 181 | 59 |
| BM 11.189 ($10^{-4}M$) | 50 | 23 |
| theophylline ($10^{-3}M$) | 100 | 66 |

For the detection of the inhibition of the heart-circulation actions of adenosine and of the adenosine derivatives according to the present invention by theophylline and its derivatives, there was determined the conduction of the heart by adenosine in guinea pigs and the removal of this effect by theophylline. There was measured the dosage of adenosine, as well as of the adenosine derivative BM 11.189, which initiated a sinus bradycardia or also an AV block and the theophylline dosage by which this can be inhibited.

1. Reduction of the ventricular frequency by BM 11.189 in the case of narcotised guinea pigs and removal of this effect by theophylline.

It was to be elucidated whether and in which dosage the adenosine derivative BM 11.189 initiated a sinus bradycardia or also AV block and whether these effects can be inhibited by theophylline as in the case of other adenosine derivatives.

Method:

The ventricular frequency of guinea pigs under urethane narcosis was recorded via an ECG lead-off by adhesive electrodes and read off after 15 seconds or 45 minutes.

The influencing of the ventricular frequency by increasing, accumulating i.v. dosages of BM 11.189 were investigated and the dosage for the frequency reduction to 120 beats/minute ($DE_{120}$) was interpolated logarithmically.

Furthermore, BM 11.189 with this $DE_{120}$ (corresponding to 6 mg./kg. i.v.) was investigated alone and with increasing, accumulating dossages of theophylline (euphylline).

In addition, 10 mg. of BM 11.189/kg were administered intravenously for the production of an AV block and there was tested whether or how strongly theophylline (euphylline 20 mg./kg. i.v.), administered prophylactically or subsequently, normalised the frequency.

Results:

FIG. 1 of the accompanying drawings shows a single example for the reduction of the ventricular frequency by BM 11.189 and the antagonism of theophylline. At a comparatively high dosage of 10 mg./kg. i.v., BM 11.189 caused an extreme reduction of the ventricular frequency which, in part, came about by a reduction of the sinus frequency and in part by an AV block. Comparable effects were initiated by L-PIA, even with dosages of from 30 to 100 mcg./kg. Euphylline completely removed the AV block and substantially removed the sinus bradycardia.

Theophylline (euphylline: 20 mg./kg. i.v.), administered not only prophylactically but also subsequently, enabled a frequency change due to BM 11.189 (10 mg./kg. i.v.) to be kept substantially in the range of the normal values or to be returned to this range (see Table 5).

TABLE 5

Influencing of the heart frequency of narcotised guinea pigs by BM 11.189 and euphylline
narcosis: urethane 1.3 g./kg. i.p.
n = 4    M ± SEM

| group | animal weight g. | $f_{cor}$ blank | 1.0 ml/kg | $f_{cor}$ 15 min. after | | $f_{cor}$ (beats/min) ... min. after administration | | | | | |
|---|---|---|---|---|---|---|---|---|---|---|---|
| | | | | | | 15 | 30 | 45 | 60 | 75 | 90 |
| I | 388 ± 16 | 273 ± 26 | NaCl 0.9% control | 252 ± 24 | BM 11.189 10 mg/kg i.v. | 88 ± 15 | 152 ± 35 | 163 ± 32 | 139 ± 24 | 207 ± 10 | 212 ± 16 |
| II | 376 ± 28 | 267 ± 20 | euphylline 20 mg/kg i.v. | 319 ± 8 | | 250 ± 14 | 265 ± 7 | 269 ± 8 | 282 ± 11 | 278 ± 14 | 284 ± 6 |
| III | 346 ± 20 | 306 ± 37 | BM 11.189 10 mg/kg i.v. | 91 ± 35 | euphylline 20 mg/kg i.v. | 231 ± 36 | 262 ± 36 | 282 ± 25 | 280 ± 29 | 286 ± 31 | 292 ± 26 |
| IV | 350 ± 15 | 277 ± 18 | NaCl 0.9% control | 251 ± 16 | | 284 ± 12 | 297 ± 15 | 302 ± 17 | 304 ± 12 | 306 ± 11 | 307 ± 8 |

2. Antagonism between theophylline derivatives and adenosine.

Method:

Adenosine was injected in amounts of 0.5 mg./kg. at 10 minute intervals into guinea pigs under urethane narcosis. This produced an atrioventricular block, whereby the frequency of the heart chamber decreased by more than 200 beats per minute.

After 2 control injections, logarithmically increasing dosages of the xanthine derivatives to be tested were injected, the total dosage thereby being doubled in the case of each injection. The initial dosage was 1.25 mg./kg. in the case of euphylline and 5 mg./kg. in the case of the other substances. The decrease of the ventricular frequency under adenosine was plotted against the logarithm of the dosage and the dosage was calculated which reduced the bradycardia by adenosine by 50% ($DE_{50}$).

10 minutes after the last injection of adenosine, there were injected 10 mg./kg. BM 11.189.

Results (Table 6):

The chosen experimental protocol made it possible to quantify the effectiveness of the theophylline derivatives. As an average of 6 experiments, 9.8 mg./kg. euphylline was required in order to reduce to a half the decrease of the ventricular frequency caused by adenosine. The highest dosage of euphylline amounted, in 4 experiments, to 20 mg./kg. and in the other two to 40 mg./kg. Thereafter, adenosine only further decreased the chamber frequency by 22 beats per minute.

8-Chlorotheophylline first inhibits the bradycardia in comparatively high dosages ($ED_{50}$: 127 mg./kg.; n=4). However, its action maximum was not lower than that of adenosine. After a total of 320 mg./kg., adenosine further reduced the chamber frequency on average by only 11 beats per minute.

Theophylline isobutanolamine was about half as effective as euphylline.

TABLE 6

Antagonism of theophylline derivatives towards the action of adenosine and BM 11.189 on the heart

| test substance | initial frequency | reduction of the heart frequency (beats/min.) by adenosine | | $DE_{50}$ mg/kg | BM 11.189 frequency decrease |
|---|---|---|---|---|---|
| | | control | end of experiment | | |
| euphylline | 280 | 222 | 22 | 9.80 | 36 |
| 8-chlorotheo-phylline | 273 | 222 | 11 | 127 | 14 |
| theophylline isobutanol-amine | 281 | 236 | 29 | 20.5 | 68 |

Since the anti-allergic action is not inhibited by the administration of these theophylline or xanthine derivatives but rather, on the contrary, even strengthened, such a combination displays practically only the anti-allergic action and is, therefore, especially advantageous for the treatment of inflammatory and allergic diseases, for example bronchial asthma.

Therefore, the present invention is also concerned with the use of a combination of adenosine derivatives of general formula (I) with xanthine derivatives of the general formula:

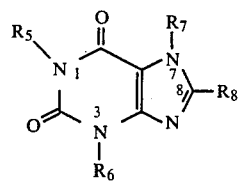

wherein $R_5$ is a hydrogen atom or a lower alkyl or alkenyl radical, $R_6$ is a hydrogen atom, a lower alkyl radical which can be substituted by hydroxyl or a lower alkenyl radical, $R_7$ is a hydrogen atom or an alkyl radical which can be substituted by halogen and $R_8$ is a hydrogen or halogen atom, an amino or nitro group, a lower alkyl radical which can be substituted by hydroxyl, halogen or phenyl, a lower alkylthio or alkoxy radical, a mono- or dialkylated amino group, a cycloalkyl radical or an aryl radical which can be substituted one or more times by halogen, alkyl, alkoxy, nitro, amino, carboxyl, hydroxyl or mono- or dialkylated amino, for the treatment of allergic diseases, as well as of bronchospastic and bronchoconstrictive reactions brought about by inflammation.

The compounds of general formula (II) are known compounds.

By a lower alkyl radical of the substituents $R_5$, $R_6$, $R_7$ and $R_8$ are to be understood radicals with up to 6 carbon atoms and preferably methyl, ethyl, n-propyl, isopropyl and n-hexyl radicals.

A lower alkylthio radical contains up to 6 carbon atoms and is preferably the methylthio radical.

A lower alkoxy radical contains up to 6 carbon atoms and is preferably a methoxy or ethoxy radical.

A lower alkenyl radical contains 2 to 6 carbon atoms and is preferably the allyl radical.

By halogen there are to be understood fluorine, chlorine, bromine and iodine, fluorine, chlorine and bromine being preferred.

An aryl radical of the substituents $R_8$ is a phenyl or naphthyl radical, the phenyl radical being preferred.

Preferred xanthine derivatives of general formula (II) are compounds in which $R_5$ is a hydrogen atom or a $C_1$–$C_4$ alkyl radical, $R_6$ is a hydrogen atom or a $C_1$–$C_4$ alkyl radical, $R_7$ is a hydrogen atom or a $C_1$–$C_4$ alkyl radical and $R_8$ is a hydrogen or halogen atom, a $C_1$–$C_4$ alkyl radical or an optionally substituted phenyl radical, the especially preferred compounds being theophylline and 8-chlorotheophylline.

The present invention also provides pharmaceutical compositions which contain at least one compound of general formula (I) or (I') and conventional carrier materials.

Furthermore, the present invention also provides pharmaceutical combinations which, besides the conventional carrier and adjuvant materials, contain, as active components, a compound of general formula (I) or (I') and a compound of general formula (II). The two active materials, an adenosine derivative of general formula (I) or (I'), as well as a xanthine derivative of general formula (II), are, as a rule, present in the combination in a ratio of from 2:1 to 1:20 and preferably of 1:10.

For the production of pharmaceutical agents, the compounds of general formula (I) or (I') and optionally compounds of general formula (II) are mixed in known manner with appropriate pharmaceutical carrier substances and possibly granulated and pressed, for example, into tablets or dragee cores. It is also possible to fill the mixture into hard gelatine capsules. With the addition of appropriate adjuvants, there can also be produced a solution or suspension in water, an oil (for example olive oil) or high molecular weight polymer (for example polyethylene glycol) and worked up to give injection solutions, soft gelatine capsules, syrups or drops.

The compounds of general formulae (I), (I') and (II) can be administered orally or parenterally in liquid or solid form. As injection medium, it is preferred to use water which contains the stabilisers, solubilisers and/or buffers conventional in the case of injection solutions. Additives of this kind are, for example, tartrate and borate buffers, ethanol, dimethyl sulphoxide, complex formers (such as ethylenediamine-tetraacetic acid), high molecular weight polymers (such as liquid polyethylene oxide) for viscosity regulation and polyethylene derivatives of sorbitan anhydrides.

Solid carrier materierals are, for example, starch, lactose, mannitol, methyl cellulose, talc, highly dispersed silicic acid and high molecular weight polymers, such as polyethylene glycols.

Compositions suitable for oral administration can, if desired, contain flavouring and sweetening materials. For external application, the compounds according to the present invention of general formula (I) or (I'), optionally in admixture with a compound of general formula (II), can also be used in the form of powders or salves. For this purpose, they are mixed, for example, with powdered physiologically compatible diluents or conventional salve bases.

The dosage administered depends upon the age, the state of health and the weight of the recipient, the extent of the disease, the nature of further treatments possibly carried out simultaneously, the frequency of the treatments and the nature of the desired action. Usually, the daily dosage for an adult is 120 mg. per adenosine derivative and up to 60 mg. per xanthine derivtive. Normally, individual dosages of 10 to 40 and preferably of from 30 to 120 mg. per day in one or more applications per day are effective in order to achieve the desired results.

An appropriate form of administration consists of 10 to 20 mg. of BM 11.189 as adenosine derivative and 235 mg. of euphylline as xanthine derivative, as well as appropriate carrier materials and is produced in the form of 300 mg. tablets which, as a rule, are taken orally three times a day.

It will be understood that the specification and examples are illustrative but not limitative of the present invention and that other embodiments within the spirit and scope of the invention will suggest themselves to those skilled in the art.

We claim:

1. Compound of the formula:

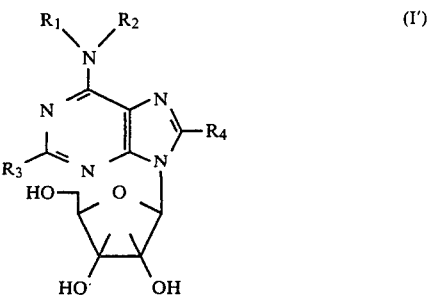

wherein $R_1$ is a hydrogen atom or a $C_1$-$C_8$ alkyl or hydroxyethyl radical, $R_2$ is a hydrogen atom or a $C_1$-$C_8$ alkyl, benzyl, hydroxethyl or cyclohexyl radical or $R_1$ and $R_2$, together with the nitrogen atom to which they are attached, form a piperidino or morpholino ring, $R_3$ is a hydrogen atom, an amino group or a benzyl amino radical optionally substituted by a methyl radical or is a morpholino or piperidino radical and $R_4$ is a benzylamino, morpholino or piperidino radical and, when $R_3$ is a morpholino or piperidino radical, $R_4$ can also be a hydrogen atom and a pharmacologically acceptable salt thereof.

2. A pharmaceutical composition for the treatment of allergic diseases, as well as of bronchospastic and bronchoconstrictive reactions brought about by inflammation, containing an adenosine derivative of claim 1 and a xanthine derivative of the formula:

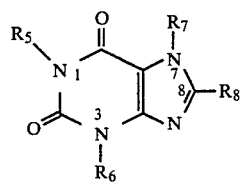

wherein $R_5$ is a hydrogen atom or a lower alkyl or alkenyl radical, $R_6$ is a hydrogen atom, a lower alkyl radical which can be substituted by hyroxyl or a lower alkenyl radical, $R_7$ is a hydrogen atom or a lower alkyl radical which can be substituted by halogen and $R_8$ is a hydrogen or halogen atom, an amino or nitro group, a lower alkyl radical which can be substituted by hydroxyl, halogen or phenyl, a lower alkylthio or alkoxy radical, a mono- or dialkylated amino group a cycloalkyl radical or an aryl radical which can be substituted one or more times by halogen, alkyl, alkoxy, nitro, amino, carboxyl, hydroxyl, or mono- or dialkyl-amino group and a pharmaceutically acceptable carrier.

3. A pharmaceutical composition for the treatment of allergic diseases, as well as of bronchospastic and bronchoconstrictive reactions caused by inflammation, comprising a compound according to claim 1 and a pharmaceutically acceptable carrier.

4. A method of treatment of allergic diseases, and bronchospastic and bronchoconstrictive reactions brought about by inflammation, comprising applying an effective amount of adenosine derivatives of the general formula:

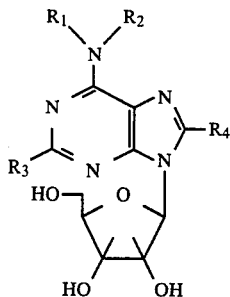

(I)

wherein $R_1$ and $R_2$, which can be the same or different, are straight-chained or branched alkyl radicals which can be substituted one or more times by hydroxyl, alkoxycarbonyl, or alkoxy groups, by phenalkyl or alkyl-substituted amino groups, whereby the phenyl moiety can also be be substituted, by aryl, heteroaryl or aryloxy radicals optionally substituted one or more times by hydroxyl, alkoxy, alkyl, trifluoromethyl, halogen, amino or methylsulphonamino, or by cycloalkyl, which can be annelated with an aryl ring; or $R_1$ and $R_2$ are straight-chained or branched alkenyl radicals or $R_1$ and $R_2$ are saturated or unsaturated cyclic aliphatic radicals which can be annelated with an aryl ring, or $R_1$ and $R_2$, together with the nitrogen atom to which they are attached, can form a heterocyclic ring which can be optionally interrupted by a further oxygen, sulphur or nitrogen atom, which nitrogen atom can be substituted by alkyl or aralkyl, $R_3$ is a hydrogen or halogen atom, a hydroxyl group, an alkoxy, morpholino or piperidino radical or an amino group which can optionally be substituted by alkyl or optionally substituted aralkyl and $R_4$ is a hydrogen or halogen atom or a morpholino or piperidino radical or an amino group optionally substituted by alkyl or aralkyl and one of the symbols $R_1$ and $R_2$ can also represent a hydrogen atom, with the proviso that the other symbol is not a phenylisopropyl radical, as well as a pharmacologically compatible salt.

5. A method according to claim 4, wherein wherein $R_3$ and $R_4$ are hydrogen atoms.

6. A method according to claim 5 wherein $R_1$ and $R_2$ do not signify hydrogen atoms.

7. A method of treatment of allergic diseases, and bronchospastic and bronchoconstrictive reactions caused by inflammation comprising applying an effective amount of adenosine derivatives of claim 4 together with xanthine derivatives of the general formula:

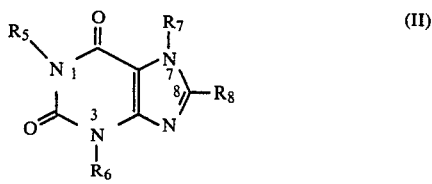

(II)

wherein $R_5$ is a hydrogen atom or a lower alkyl or alkenyl radical, $R_6$ is a hydrogen atom, a lower alkyl radical which can be substituted by hydroxyl or a lower alkenyl radical, $R_7$ is a hydrogen atom or a lower alkyl radical which can be substituted by halogen and $R_8$ is a hydrogen or halogen atom, an amino or nitro group, a lower alkyl radical which can be substituted by hydroxyl, halogen or phenyl, a lower alkylthio or alkoxy radical, a mono- or dialkylated amino group, a cycloalkyl radical or an aryl radical which can be substituted one or more times by halogen, alkyl, alkoxy, nitro, amino, carboxyl, hydroxyl or mono- or dialkylated amino group.

* * * * *